United States Patent [19]
Dean et al.

[11] Patent Number: 5,843,662
[45] Date of Patent: Dec. 1, 1998

[54] METHOD, DEVICE, AND KIT FOR TOTAL NUCLEIC ACID ASSAY

[75] Inventors: Alan Dean; Aftab Alam, both of St. Louis, Mo.

[73] Assignee: Geno Technology, Inc., St. Louis, Mo.

[21] Appl. No.: 645,142

[22] Filed: May 13, 1996

Related U.S. Application Data

[63] Continuation-in-part of Ser. No. 370,685, Jan. 10, 1995, abandoned, and Ser. No. 564,709, Nov. 29, 1995.

[51] Int. Cl.$^6$ ..................................................... C12Q 1/68
[52] U.S. Cl. .............................. 435/6; 435/975; 536/23.1; 436/94
[58] Field of Search ....................... 435/6, 975; 536/23.1; 436/94

[56] References Cited

U.S. PATENT DOCUMENTS 4,677,054  6/1987  White et al. .
4,898,951  2/1990  Symons .

OTHER PUBLICATIONS

Sambrook "Molecular Cloning: a Laboratory Manual" 2nd Edition (1987) Cold Spring Harbor Laboratory Press, USA pp. E.5–E.6.
Thomas *PNAS* (1980) 77(9) pp. 5201–5205.
Kimmel, "Guide to Molecular Cloning Techniques" Academic Press, Inc, USA, pp. 71 and 576, 1987.

*Primary Examiner*—Paula K. Hutzell
*Assistant Examiner*—Heather A. Bakalyar

[57] ABSTRACT

A method, device and a kit for determining total nucleic acid concentration in a nucleic acid solution, which comprises applying the nucleic acid solution to a nucleic acid-support capable of retaining the total nucleic acid in the form of a nucleic acid spot having a size that is proportional to the nucleic acid concentration; measuring the size of the nucleic acid spot produced on the nucleic-support; and comparing the size of the nucleic acid spot with a standard.

19 Claims, 5 Drawing Sheets

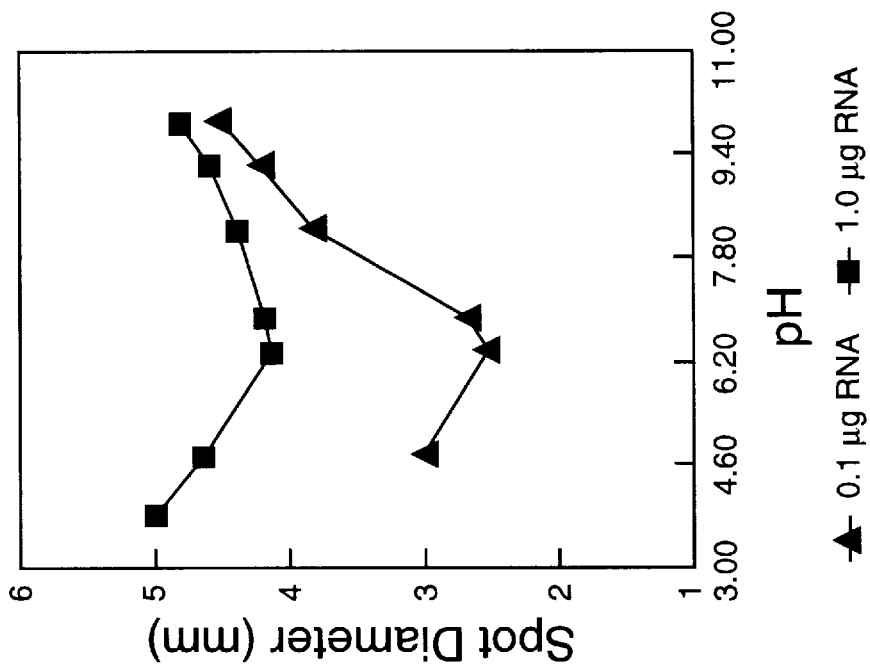
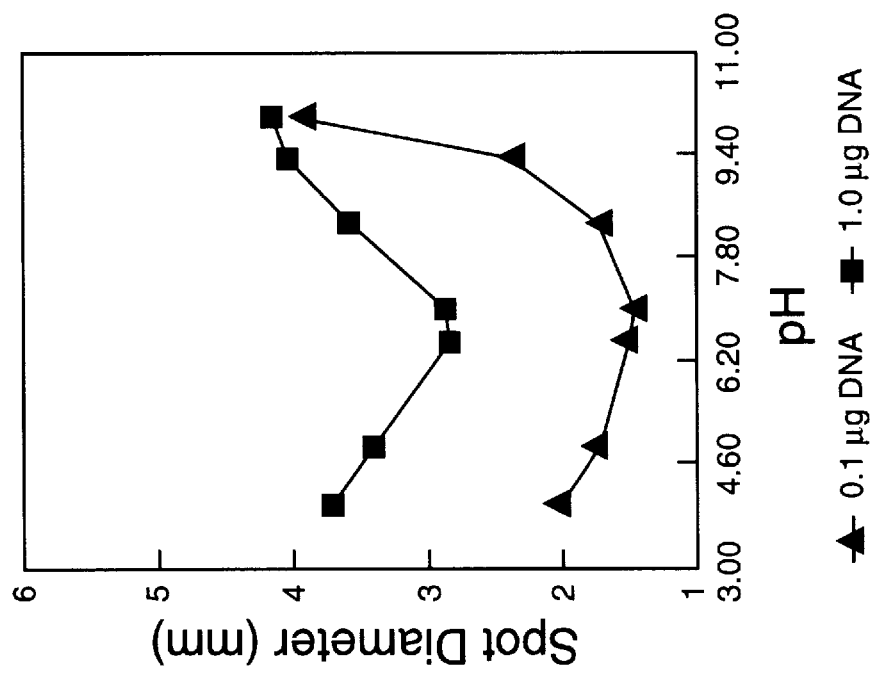

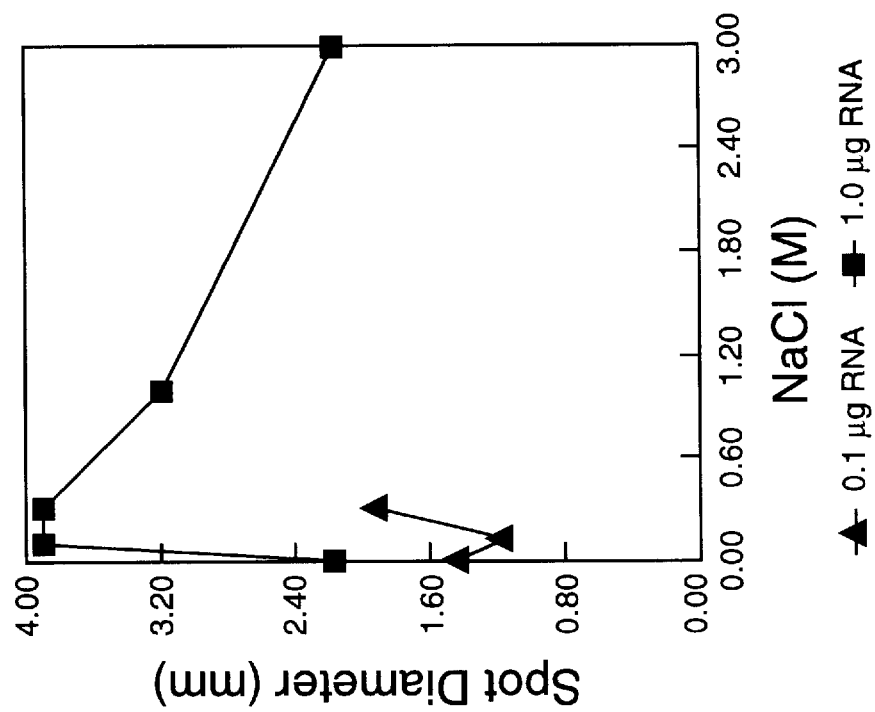
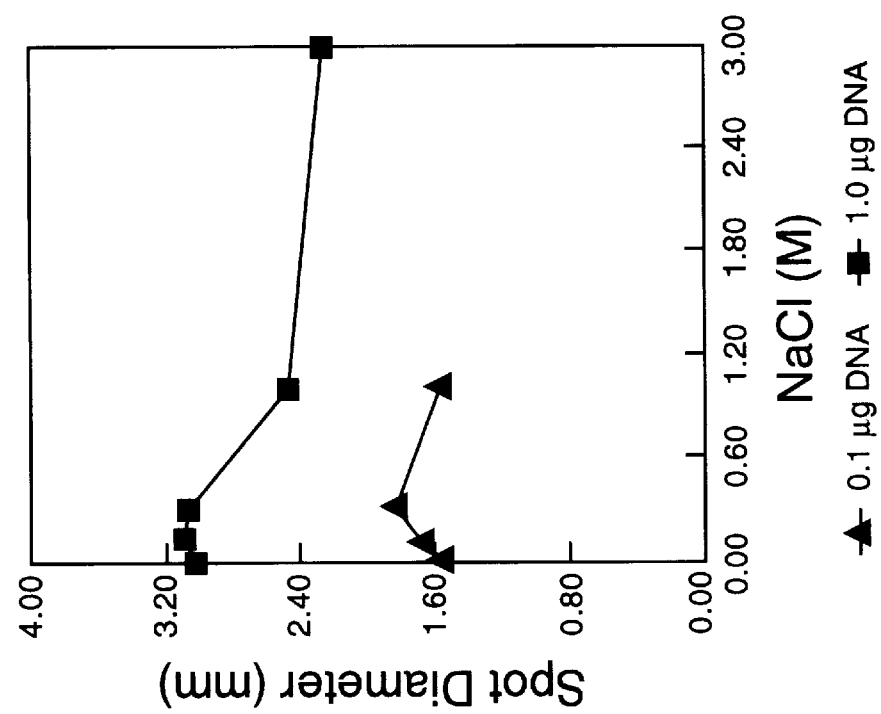

METHOD, DEVICE, AND KIT FOR TOTAL NUCLEIC ACID ASSAY

CROSS-REFERENCE TO RELATED APPLICATIONS

This application is a continuation-in-part of Applicant's U.S. patent applications Ser. No. 08/370,685, filed Jan. 10, 1995, now abandoned, and Ser. No. 08/564,709, filed Nov. 29, 1995 which are incorporated herein in its entirety by reference.

BACKGROUND OF THE INVENTION

1. Field of the Invention

This invention relates to a method, device and kit for estimation of total nucleic acid in a sample.

2. Description of the Related Art

The U.S. patent application Ser. No. 08/370,685 (abandoned) and the continuation-in-part thereof describe a method of protein assay particularly but not exclusively. The invention involves applying a small aliquot of a protein solution to a test strip or support membrane to produce a compact protein spot of a size that is substantially proportional to the concentration of protein in the protein solution. This proportional relationship allows the concentration of protein in a sample to be determined. The present invention is a further improvement and expansion on the principles of the invention described in the above indicated patent applications.

Estimation of nucleic acid is essential for biological research as well as in some clinical diagnostics. The standard and accepted method of estimation of nucleic acids is by measurement of optical density at 260 nm using a spectrophotometer. Unfortunately, spectrophotometric analysis is time consuming and also requires use of expensive equipments. There are kits available for rapid estimation of nucleic acid which use test strips. Nucleic acid samples are applied to the test strip and strip is developed to detect nucleic acid spots on the test strip. For estimation of nucleic acid concentration the color intensity of the nucleic acid spot is compared with a color chart of predetermined concentration of nucleic acid spots. Such methods for estimation of nucleic acid concentration are not reliable and it is also not convenient to compare the color of nucleic acid spots. There are two such kits currently in the market, one of such kit is offered by Kodak Chemical Company, New Haven, Conn., USA. and another kit is offered by Invitrogen, CA. USA. Therefore, there is a need for developing a method, device and a kit for rapid and non-spectrophotometric estimation of nucleic acid which is more reliable than the kits presently available.

SUMMARY OF THE INVENTION

The present invention provides a method, device and kit for determination of total nucleic acid concentration, or nucleic acid assay, in a sample. As used herein, nucleic acid refers to nucleic acid in general and is not limited to nucleic acid having any particular characteristics and includes both single and double stranded nucleic acids, such DNA, RNA as well as synthetic oligonucleotides (Oligos). Total nucleic acid means all the nucleic acid that is present in a sample. Thus, the nucleic acid assay of the invention is useful to determine total nucleic acid concentration in samples having only one type of nucleic acid as well as samples having a mixture of different nucleic acids.

Accordingly, the invention provides a method for determining total nucleic acid concentration in a nucleic acid solution, which comprises: applying the nucleic acid solution to a porous nucleic acid-support capable of retaining the nucleic acid in the form of a nucleic acid spot, wherein the nucleic acid contacts the nucleic acid-support in the presence of an aqueous medium having a pH effective to form a substantially uniform nucleic acid spots having a size that is proportional to the nucleic acid concentration; measuring the size of the nucleic acid spot produced on the nucleic acid-support; and comparing the size of the nucleic acid spot with a standard.

The present invention also provides a device, hereinafter referred to as a nucleic acid gauge, for determining an unknown amount of total nucleic acid in a substantially circular nucleic acid spot on a nucleic acid-support, which comprises a display showing a substantially linear relationship between spot diameter and nucleic acid amount for at least two substantially circular standard spots containing known, different amounts of nucleic acid produced on the nucleic acid-support.

The invention is also directed to a kit for determining the concentration of total nucleic acid in a nucleic acid solution, which comprises: a porous nucleic acid-support for retaining the nucleic acid from the nucleic acid solution applied to the nucleic acid-support, wherein the nucleic acid-support is capable of retaining the nucleic acid in the form of a substantially circular nucleic acid spot when the nucleic acid contacts the nucleic acid-support in the presence of an aqueous medium having a pH effective to form a substantially uniform nucleic acid spots having a size that is proportional to the nucleic acid concentration; a nucleic acid gauge for determining an unknown amount of nucleic acid in the nucleic acid spot, wherein the gauge shows a substantially linear relationship between the diameter of the nucleic acid spot and the amount of nucleic acid in the spot; preferably, a dilution solution for preparing the nucleic acid solution from a sample to be measured; and a reagent solution for visualizing the nucleic acid spot on the nucleic acid-support.

The invention will be better understood by reference to the following detailed description of preferred embodiments of the invention and the drawings that form part of this specification.

BRIEF DESCRIPTION OF THE DRAWINGS

FIGS. 7A and 7B show two plots A and B illustrating the effects of pH on the spot formation on a nucleic acid-support for DNA (plot-A) and RNA (plot-B).

FIGS. 8A and 8B show two plots A and B illustrating the effects of salt concentration on the spot formation on a nucleic acid-support for DNA (plot-A) and RNA (plot-B).

DESCRIPTION OF THE PREFERRED EMBODIMENTS

Figure 1:
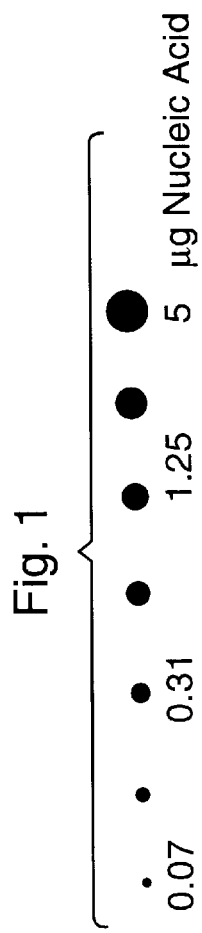
FIG. 1 shows an actual print of nucleic acid spots produced by applying nucleic acid solutions of various concentrations to a nucleic acid-support in accordance with the invention; the print illustrates the proportional relationship between the amount of nucleic acid in a nucleic acid spot and the diameter of the nucleic acid spot.

Determining the concentration of total nucleic acid in a nucleic acid solution in accordance with the invention comprises applying the nucleic acid solution to a porous nucleic acid-support in the presence of an aqueous medium or solution having a pH effective to form a substantially uniform nucleic acid spot having a size that is proportional to the nucleic acid concentration; measuring the size of the nucleic acid spot on the nucleic acid-support; and comparing the size of the nucleic acid spot with a standard.

The nucleic acid-support is capable of retaining the nucleic acid in the form of a substantially uniform nucleic acid spot having a size that is proportional to the total nucleic acid concentration in the solution. The nucleic acid spot may have any shape whose size is capable of being measured quantitatively. For example, the nucleic acid spot may have a circular, rectangular, or any other geometric shape for which well-known size measurements exist, provided the nucleic acid being measured is spread substantially uniformly throughout the shape of the spot. The spot size measured may include, but is not limited to, diameter, area, circumference, density, or volume of the shape produced. Preferably, the nucleic acid-support is capable of producing nucleic acid spots that are substantially circular in shape having diameters that are substantially proportional to the concentration of total nucleic acid in the solution.

The nucleic acid-support may comprise a porous membrane such as, nylon and other types of nucleic acid binding membranes well-known in the art. Preferably, the nucleic acid-support comprises a nylon membrane. More preferably, the nucleic acid-support is a positively charged nylon membrane. Most preferably, the positively charged nylon membrane is the one supplied by Micron Separation Inc (MSI), Westboro, Mass., USA. (1995–96 Catalogue), under the trade name MAGNACHARGE nylon membranes. The pore size of the nucleic acid-support is large enough to provide sufficient capillary wicking action to produce substantially uniform nucleic acid spots whose sizes vary proportionally with nucleic acid concentration to an extent that can be reliably measured. Preferably, the pore size is larger than 0.05 $\mu$m (micron). More preferably, the pore size of the nucleic acid-support is 0.2 $\mu$m (micron) or larger. Most preferably, the nucleic acid-support has a pore size of approximately 0.45 $\mu$m (micron).

The nucleic acid-support is preferably large enough to allow complete diffusion of the nucleic acid solution applied to it without the nucleic acid solution reaching the edges of the nucleic acid-support. For example, a 1 $\mu$l solution applied to a nucleic acid-support according to the invention would generally spread 6–7 mm outward from the point of application; therefore, the nucleic acid-support is preferably wider than 7≧8 mm so that the spreading solution does not reach its edges.

The volume of nucleic acid solution applied to the nucleic acid-support is preferably maintained constant, at about 1–10 $\mu$l per spot. Most preferably, the volume of nucleic acid solution applied to the nucleic acid-support is 1—5 $\mu$l. The nucleic acid solution is preferably applied to the nucleic acid-support in such a manner to allow the solution to diffuse slowly out of the pipetor tip into the nucleic acid-support, i.e., preferably through capillary action; forcibly expelling the nucleic acid solution onto the nucleic acid-support is not recommended.

To promote formation of nucleic acid spots that are proportional to the concentration of total nucleic acid in the nucleic acid solution applied to the nucleic acid-support, the nucleic acid contacts the support membrane in the presence of an aqueous solution or medium having a pH that is effective in formation of a substantially uniform nucleic acid spot having a size that is proportional to the nucleic acid concentration. Preferably, nucleic acid contact the nucleic acid-support in the presence of an aqueous medium having a pH from 4–9. More preferably, nucleic acid DNA contact the nucleic acid-support in the presence of an aqueous medium having a pH from 4.5–8.5, and RNA and/or Oligos contact the nucleic acid-support in the presence of an aqueous medium having a pH 4.5–7.5. Most preferably, nucleic acid contact the nucleic acid-support in the presence of an aqueous medium having a pH from 6.5–7.5for DNA, and pH from 6.5–7.0 for RNA and/or Oligos.

Preferably, this linear relationship exists for nucleic acid spots having between 0.001 $\mu$g to 10 $\mu$g nucleic acid, and most preferably, for spots having between 0.01 $\mu$g to 5 $\mu$g nucleic acid.

The nucleic acid spots produced on the nucleic acid-support may be detected either by physical or chemical means. Such means include methods for detecting nucleic acids bound to a membrane which are currently known to those skilled in the art or any such methods developed in the future. For example, nucleic acid spots may be detected by staining the nucleic acid-support with a dye such as the nuclear dyes hematoxylin, brilliant cresyl blue or methylene blue, acridine orange, basic fuchsin or pyronine. Alternatively, the nucleic acid spots may be detected with the aid of chemically coupled reactions such as chemiluminescent reactions or immunochemical reactions. More preferably, the nucleic acid spots are detected with methylene blue dye or brilliant cresyl blue. Most preferably the nucleic acid spots are detected with methylene blue, preferable made in 20% ethanol containing 0.1M sodium acetate.

Before applying the nucleic acid solution to the nucleic acid-support, the nucleic acid solution is preferably mixed with a dilution solution, the dilution solution is an aqueous solution having a pH preferably from 4 to 9. Preferably, the dilution solution for mixing with RNA and/or Oligos has a pH from pH 6.5 to 7.5. The dilution solution for mixing with DNA solution is an aqueous solution having a pH preferably from 4.5 to 8.5. More preferably, the dilution solution for mixing with DNA has a pH from 6.5 to 8.5. Most preferably, the dilution solution has a pH around 7.0 for mixing with DNA and pH around 6.5 for mixing with RNA and/or Oligos. It should be evident to the skilled artisan that these pH specifications may changed as salt or other agents are added to the dilution solutions.

The dilution solution may also contain a salt. Salt concentration may be such that to promote formation of substantially uniform nucleic acid spot having a size that is proportional to the nucleic acid concentration. Salts which are operable in the invention include, but not limited to, sodium, potassium, and other salts. Preferably, sodium salts are used. Preferably, the salt concentration in dilution solution may be such that nucleic acid contact the nucleic acid-support in the presence of a salt concentration below 1M NaCl for DNA and below 0.5M NaCl for RNA and/or Oligos. More preferably, the salt concentration in the dilution solution is under 0.3N NaCl for mixing with nucleic acids. Most preferably, the salt concentration in the dilution solution is around 0.1M sodium acetate for mixing with DNA.

It should be evident to the skilled artisan that the pH and salt concentration in which nucleic acids DNA, RNA and Oligos contact the nucleic acid-support may be adjusted in order to increase or decrease the size of DNA, RNA or Oligos spots formed on the nucleic acid-support. In one preferred embodiment of the invention, the concentration of salt and/or pH of the aqueous medium in which nucleic acid contact the nucleic acid-support and/or the dilution solution are those which allow the nucleic acid solution to form a substantially uniform nucleic acid spot on the nucleic acid-support wherein the size of DNA, RNA and Oligos spots; are substantially identical for a selected concentration. The salt concentration and/or pH of the aqueous medium and/or the dilution solution which achieve this preferred spot forming combination is referred to as the spot-sizing combination. Preferably, there are one or more dilution solutions for nucleic acids DNA, RNA and Oligos. For example, in one preferred embodiment of the invention, two dilution solutions may be used for spot-sizing combination, such as a dilution solution having a pH 6.5 for both RNA and Oligos and a second dilution solution having a pH 7.0 for DNA solution to form substantially identical spots on the nucleic acid-support for all three DNA, RNA and Oligos at a selected concentration.

In order to improve the accuracy of the nucleic acid assay method and overcome interference by chemical agents present in a nucleic acid sample, preferably more than one nucleic acid spot is produced from each test sample. For example, a plurality of spots may be produced from one nucleic acid solution and the nucleic concentration in the solution is determined either from the average size of at least two spots or by averaging the concentrations determined from at least two spots.

Preferably, the concentration of total nucleic acid in a sample is determined from measuring the sizes of a plurality of nucleic acid spots produced from serial dilutions of the sample using dilution solution. The serial dilutions are preferably carried out in such a way that each successive dilution is 2-, 3-, or 5-fold more diluted than the previous dilution. Nucleic acid solution from each dilution is applied to the nucleic acid-support and the nucleic acid concentration in the sample is preferably determined by averaging the concentration determined from at least two of the nucleic acid spots. Preferably, each spot represents a different dilution of the sample in dilution solution.

When selecting which nucleic acid spots to measure for determining nucleic acid concentration, substantially uniform nucleic acid spots of higher-fold dilutions are preferred over nonuniform spots or nucleic acid spots of lower-fold dilutions. When measuring the diameter of the selected nucleic acid spots, each spot is preferably measured more than one time and each time a different cross-sectional diameter is preferably measured.

Once the size of a nucleic acid spot is measured, the amount of nucleic acid in the spot is determined by comparing the size of the spot to a standard. The standard shows a proportional relationship between known, but different amounts of a standard nucleic acid contained in a plurality of spots produced according to the invention and the spot sizes thereof. The standard nucleic acid may be any type of soluble nucleic acid, such as DNA, RNA or oligonucleotides. It will be understood by those of ordinary skill in the art that the spots in the standard are similarly shaped as the unknown spot and that the type of size measurement, e.g., diameter, area, etc., is the same for the standard spots and unknown spots.

Preferably, the standard is a nucleic acid gauge which displays a substantially linear relationship between spot diameter and nucleic acid amount in substantially circular nucleic acid spots produced from nucleic acid solutions of known concentration in accordance with the invention. For example, the nucleic acid gauge may be in the form of a table or graph which relates the diameter of nucleic acid spots to the known amounts of nucleic acid in those spots. The nucleic acid gauge may also include means for measuring the size of the nucleic acid spots.

The concentration (i.e., $\mu g/\mu l$) of total nucleic acid in the original sample may then be calculated by dividing the amount of nucleic acid (i.e., $\mu g$) in a measured spot by the volume of nucleic acid solution (i.e., $\mu l$) applied to form the spot and then multiplying by the dilution factor, if any, for that nucleic acid spot.

Another object of the present invention is to provide a nucleic acid gauge useful for determining the amount of nucleic acid contained in nucleic acid spots produced according to the above described method. The nucleic acid gauge comprises a display showing a substantially linear relationship between spot diameter and nucleic acid amount for at least two standard substantially circular standard spots containing known, different amounts of a standard nucleic acid. Preferably, the display shows a substantially linear relationship between spot diameter and nucleic acid amount for standard spots containing from about 0.025 $\mu g$ to about 10.0 $\mu g$ nucleic acid. More preferably, the display shows spot diameters ranging from about 0.5 mm to about 6 mm for standard spots containing from about 0.01 $\mu g$ to about 5.0 $\mu g$ nucleic acid, respectively.

The substantially linear relationship between size and nucleic acid amount for the standard spot may be the result of any type of chemistry currently known or developed in the future. Preferably, the chemistry producing this relationship is the method described above, i.e., the standard nucleic acid spots are produced in the same manner as the sample nucleic acid spots.

Figure 3:
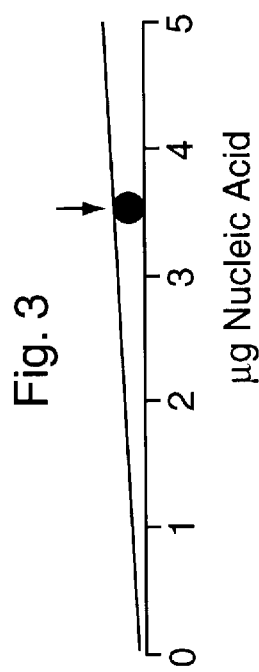
FIG. 3 shows a first embodiment of a nucleic acid gauge based on the plot of FIG. 2 for determining the amount of nucleic acid in nucleic acid spots produced on a nucleic acid-support in accordance with the invention, also shows the use of nucleic acid gauge.
Figure 6:
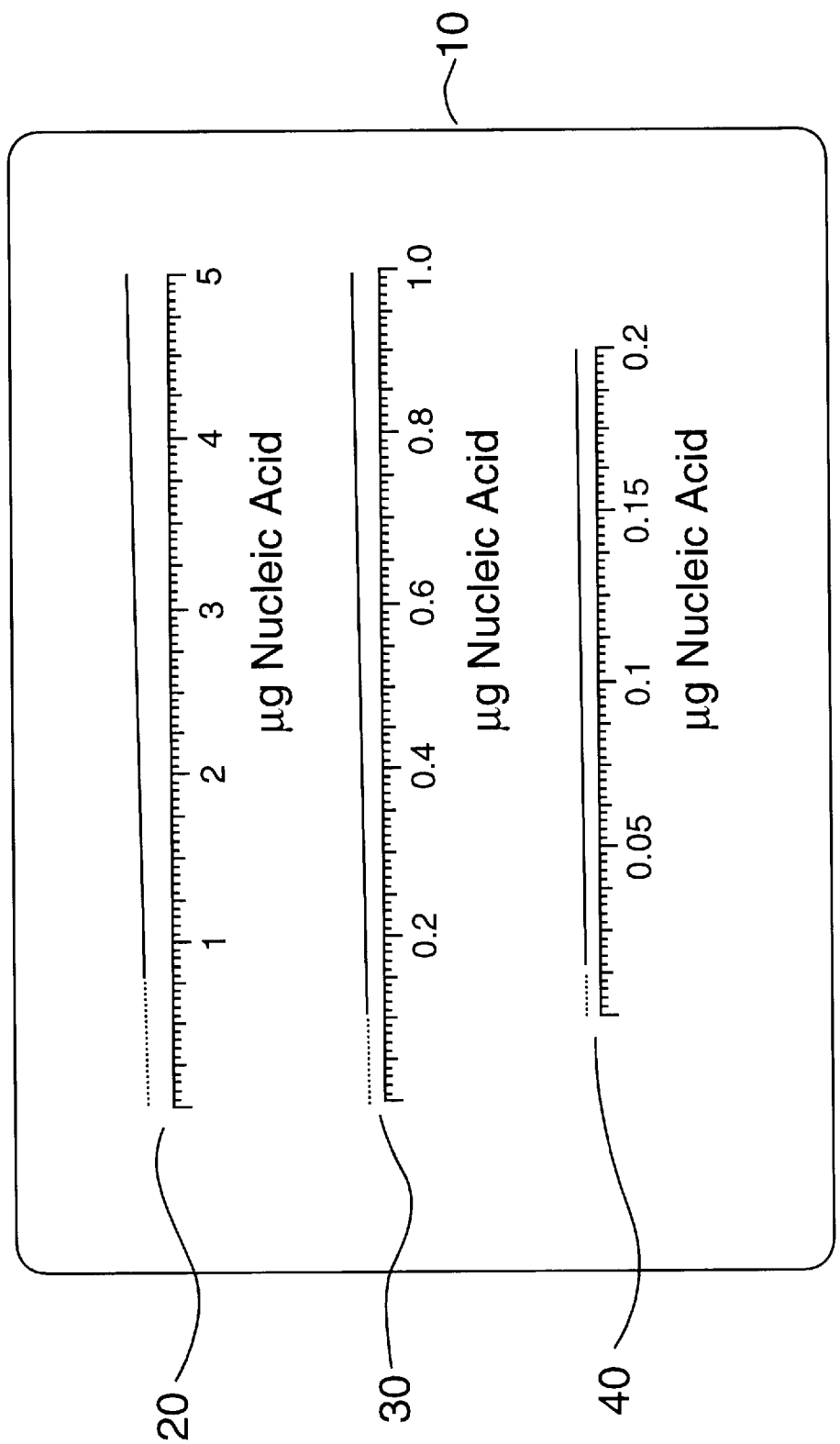
FIG. 6 shows a third embodiment of the nucleic acid gauge which is derived from the plots of FIG. 5.

In the preferred embodiment, the display of the nucleic acid gauge has means for simultaneously measuring the diameter of the nucleic acid spot and comparing this measurement to the substantially linear relationship exemplified by the display. As shown in FIG. 3, the means for simultaneously measuring and comparing preferably comprises at least one wedge-shaped display composed of first and second converging linear members, at least one of the members being graduated, and the angle of convergence between said members defines the substantially linear relationship between spot size and nucleic acid amount, and the graduated member having at least one reference mark representing a nucleic acid amount or spot diameter. The reference mark may comprise numerals, symbols, letters, words, or any other designation whose relationship with the represented amount of nucleic acid or spot diameter is known. Preferably, the display has an angle of convergence having a degree defined by a distance between the first and second linear members of about 1 mm at 0.0125 $\mu g$ of nucleic acid and about 3 mm to 6 mm at 5 $\mu g$ of nucleic acid. The nucleic acid gauge may have one display showing nucleic acid amounts in a range from 0.01 µg to 5 µg, or the gauge may have multiple wedge-shaped displays showing nucleic acid amounts in intermediate ranges between 0.01 µg and 5 µg as shown in FIG. 6. Gauges with multiple displays are useful for more precise determinations of nucleic acid concentration over a wide range of nucleic acid concentration.

The nucleic acid gauge having at least one wedge-shaped display is made by measuring the diameters of at least two standard nucleic acid spots containing known, but different amounts of a standard nucleic acid, with the spots being produced on a nucleic acid-support according to the above described method, and plotting the diameter versus nucleic acid amount, or vice versa, for each spot on an X-Y graph. The linear section of the curve generated by connecting each point on the plot that corresponds to a standard nucleic acid spot defines one of the two converging linear members of the display and has a slope which defines the angle of convergence between these converging members. The other linear member of the display is defined by the X or Y axis, and is preferably defined by the axis representing nucleic acid amounts. Preferably, the display is then transferred to a transparent sheet material, allowing the display to be placed immediately over the nucleic acid spot or spots to be measured, as shown in FIG. 3.

The nucleic acid gauge is used by placing a visible nucleic acid spot containing an unknown amount of nucleic acid on the wedge-shaped display, moving the spot along the wedge until the top and bottom boundaries of the spot just meet the interior edges of the linear members of the wedge, and then reading the spot diameter and/or nucleic acid amount from the point on the graduated linear member located immediately above or beneath the center of the circular spot. Preferably, if the nucleic acid gauge is transparent, the gauge is placed on top of the nucleic acid-support containing the nucleic acid spot to be measured and maneuvered until the display is directly over the nucleic acid spot as described above and shown in FIG. 3.

Figure 4:
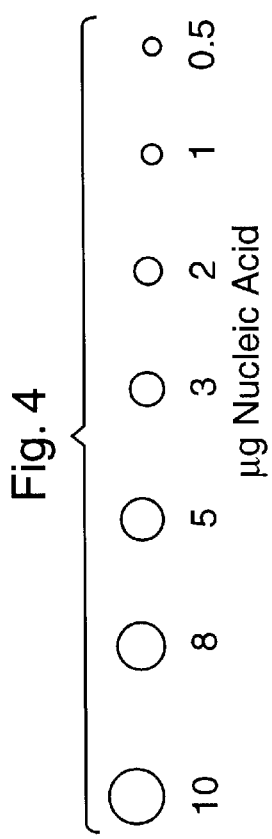
FIG. 4 shows a second embodiment of the nucleic acid gauge which contains a series of circular measuring means.

Alternatively, the means for simultaneously measuring and comparing comprises a plurality of circles as shown in FIG. 4, with the circles representing the sizes of nucleic acid spots containing known, but different amounts of a standard nucleic acid, with the spots being produced according to the method of the invention. The amount of nucleic acid in a spot being measured is estimated by comparing the diameter of the sample nucleic acid spot with the diameter of the circles.

The nucleic acid gauge may also have variable measuring means for measuring the diameter of nucleic acid spots. The variable means includes, but is not limited to, a calliper gauge.

Other types of nucleic acid gauges may be prepared as long as the nucleic acid gauge can be used for measuring the size of nucleic acid spots and has a display which shows a substantially linear relationship between nucleic acid amount and the size or diameter of nucleic acid spots. For example, the display may be a table containing information relating to the size or diameter of nucleic acid spots to corresponding nucleic acid amounts. The nucleic acid gauge may also include electronic scanning and computer software for image analysis.

Another object of the invention is to provide a kit for determining the concentration of total nucleic acid in a nucleic acid solution. The kit comprises: a porous nucleic acid-support for retaining the nucleic acid from the nucleic acid solution applied to the nucleic acid-support, wherein the nucleic acid-support is capable of retaining the nucleic acid in the form of a substantially circular nucleic acid spot when nucleic acid contacts the nucleic acid-support in the presence of an aqueous medium having a pH effective to form a substantially uniform nucleic acid spots having a diameter that is proportional to the nucleic acid concentration; a nucleic acid gauge for determining an unknown amount of nucleic acid in the nucleic acid spot, wherein the gauge shows a substantially linear relationship between the diameter of the nucleic acid spot and the amount of nucleic acid in the spot; preferably a dilution solution for preparing the nucleic acid solution from a sample to be measured; and a reagent solution for visualizing the nucleic acid spot on the nucleic acid-support.

The invention will be further explained and illustrated by the following nonlimiting examples.

EXAMPLES

Materials and Methods

Nucleic Acid-Support

Strips of the nucleic acid-support, 8 mm×80 mm, were used in all examples. Nylon membranes were obtained from Boehringer Mannheim, Germany; Hybrid, England, U.K.; Schleicher & Schuell (S&S), NH, USA and Micron Separation Inc (MSI), MA, USA. Nitrocellulose and Polyvinylidene diflouride (PVDF) membranes were obtained from MSI, MA. USA.

Nucleic Acid Solutions

Purified fractions of DNA, RNA and oligonucleotides solutions were used. 5.0–0.01 µg/µl nucleic acid solutions were applied on the nucleic acid-support.

Application of Nucleic Acid Solution to Nucleic Acid-Support

The nucleic acid solution was applied to the nucleic acid-support with a commercially available pipettor using a 0.1–10 µl preferably plastic pipet tip with an outside tip diameter of around 0.7–0.6 mm, also commercially available. The pipet tip was first wet with the nucleic acid solution by pulling 2–5 µl of the solution into the tip and then ejecting back into the solution, this process was performed once or twice. The volume on the pipettor was then adjusted to 1–5 µl and the nucleic acid solution was pulled into the tip. After making sure there was no air bubble trapped in the tip, the pipet tip was removed from the solution while touching the tip to the wall of the solution container to remove any drop of solution hanging from the tip.

The pipet tip containing the 1–5 µl aliquot of nucleic acid solution was positioned vertically over the nucleic acid-support and then lowered until the pointed end of the tip just touched the nucleic acid-support. When applying a nucleic acid solution to the nucleic acid-support, care was taken to allow the solution to diffuse slowly out of the pipetor tip into the nucleic acid-support rather than forcing the nucleic acid solution out of the tip with the pipetor plunger. Care was also taken to not move the pipet tip during the diffusion process. The application of nucleic acid solution in this manner normally took 15–20 seconds. The nucleic acid-support was then treated to detect nucleic acid spots, as described below.

Detecting Nucleic Acid Spots

The spots produced in the following examples were detected with nucleic dyes.

Aqueous solutions of Azure Blue, Basic Fuchsin, Hematoxylin, Brilliant Cresyl Blue and Methylene blue were used for detecting nucleic acid on nucleic acid-support. After applying dyes, the nucleic acid-support membrane was immersed in the dye for 30–60 seconds and then washed with de-ionized water. When methylene blue dye was used the nucleic acid-support was placed in a small dish and methylene blue dye (0.5 ml) was applied over the nucleic acid-support. The nucleic acid-support was not rocked or shaken while the dye was on the support. The dye was allowed to stand 30–60 seconds and then removed from the nucleic acid-support with a pipetor tip. The support was briefly washed with deionized water to wash away excess dye on the support. The support was removed from the wash as soon as the background disappears (30–60 seconds).

The diameters of the nucleic acid spots were measured before the nucleic acid-support was completely dry, i.e., within five minutes of removing the dye. Alternatively, a photocopy of the nucleic acid-support was made and the photocopy was used to measure the nucleic acid spots.

EXAMPLE 1

Effect of Nucleic Dye

Several nucleic acid dyes (listed above) were tested for their ability to develop nucleic acid spots into visible spots. Aqueous dye solutions were used. It was discovered that Azure Blue and Basic Fusion Blue produced high background staining resulting is poor visibility of nucleic acid spots. Hematoxylin produced clear background but the diameters of nucleic acid spots were not proportional above 1 $\mu g/\mu l$ nucleic acid. Brilliant Cresyl Blue and Methylene Blue produced desirable results i.e. no background and uniform nucleic acid spots, out of these two stains, Methylene Blue produced discreet and clear spots and thus increased sensitivity. Methylene dye was further improved by preparing the dye in 20% ethanol containing 0.1M sodium acetate, pH 7.5.

EXAMPLE 2

Effect of Membrane Type on Spot Formation

Membranes obtained from various commercial sources were tested for their suitability as the nucleic acid-support, i.e., capability of retaining nucleic acids in the form of a substantially uniform nucleic acid spot whose size is substantially proportional to the amount of nucleic acid. The nucleic acid DNA and RNA were separately dissolved in aqueous solutions having a pH from 6.7 to 7.5 and 1 $\mu l$ solution of nucleic acid was applied to various membranes. The membrane were stained with methylene blue.

The membranes tested had relatively high nucleic acid binding capacities with pore sizes of 0.05 $\mu m$ (micron) to 0.45 $\mu m$ (micron) and included nucleic acid binding membranes such as nitrocellulose, nylon and polyvinylidene diflouride (PVDF).

It was discovered that all of the positively charged nylon membranes tested retained the nucleic acid applied to it but the spot formation was not uniform for most of the membranes tested nor did the nucleic acid spots produced on the membranes had diameters or size proportional to the nucleic acid concentration. Increasing the pore size of membranes from 0.05 $\mu m$ to 0.45 $\mu m$ made no significant difference in spot formation. However, the nylon membranes obtained from MSI (Magnacharge, MSI.) behaved differed from the rest of the nylon membranes tested. Nucleic acid applied on the MAGNACHARGE nylon membrane retained the nucleic acid in the form of a nucleic acid spot having a size that was proportional to the nucleic acid concentration. Magna, a pure nylon membrane, obtained from MSI, MA, USA., behaved in a similar manner and produced nucleic acid spots proportional to the nucleic acid concentration except that when the membrane was stained with methylene blue it retained high background stain which made the measurements difficult. Nitrocellulose retained high background stain when methylene blue was used, also the nucleic acid spot were not proportional to concentration. PVDF did not retain nucleic acid applied to the membrane.

EXAMPLE 3

Effect of pH on Nucleic Acid Spot Formation

FIG. 7. show plots that illustrate the effects of pH on nucleic acid spot formation on MAGNACHARGE nucleic acid-support membrane, obtained from MSI. 1 $\mu g/\mu l$ and 0.1 $\mu g/\mu l$ DNA and RNA were separately dissolved in dilution solution having a pH from 2 to 12. The nucleic acid solution were applied to the nucleic acid-support and spots were detected with methylene blue, as described above.

It was discovered that in a pH from 4–10, nucleic acids including DNA, RNA and Oligos produced uniform nucleic acid spots that were substantially proportional in size to the nucleic acid concentration. Solutions having a pH under 4.0 or above 10.00 produced nucleic acid spots that were diffused and not proportional to nucleic acid concentration.

It was also discovered that in a pH between 6 to 8, RNA and Oligos, irrespective of their concentration, produced nucleic acid spots there were substantially identical in size. Whereas, at a pH between 6 to 8, DNA produced nucleic acid spots that were slightly smaller in size than the nucleic acid spots produced by RNA and Oligos of the same concentration. When the pH of the dilution solution was increased to pH 8–9 the size of DNA spots increased in diameter to substantially equal the size of RNA and Oligos of the same concentration. Thus by slightly adjusting the pH of the dilution solution the diameter of the DNA spots produced on the nucleic acid-support increased and substantially matched the diameter of the spots produced by RNA and/or Oligos. Such adjustment of pH could be one method of adjusting the nucleic acid spots on the nucleic acid-support, which is termed as spot-sizing. The spot-sizing pH is defined as the pH of one species of nucleic acid solution which produces nucleic acid spot on the nucleic acid-support having a size that is substantially identical in size to the nucleic acid spot of the same concentration of another species of nucleic acid solution at a different pH.

Since at a set pH, between 4–9, DNA produce spot that is smaller than spots produced by RNA and Oligos at that pH, it would require making two separate nucleic acid gauges, one for DNA and another for RNA and Oligos. By adjusting the pH of DNA solution (i.e. spot-sizing pH), it is possible to produce DNA spots identical in size to the spots produced by RNA and Oligos at a different pH. Such adjustment of pH of dilution solution eliminates the need for constructing more than one nucleic acid gauges.

EXAMPLE 4

Effect of Salt Concentration

FIG. 8 show plots illustrating the effects of salt concentration on the spot formation of DNA and RNA on MAGNACHARGE nucleic acid-support membrane. Nucleic acids DNA and RNA, concentration 0.1 $\mu g/\mu l$ and 1.0 $\mu g/\mu l$, were dissolved in the dilution solution, pH 6–7, containing 0 to 3M NaCl and applied to the nucleic acid-support. It was discovered that DNA spot formation was significantly effected by NaCl concentration above 1M NaCl and resulted in decrease of spot diameter and loss of DNA from the membrane at lower concentration. Salt concentration below 1M NaCl, the DNA spot size increase with the decreasing salt concentration. RNA spot formation was even more sensitive to salt concentration. Salt concentration above 0.3M NaCl has adverse effect on the spot formation for RNA and resulted in steep decline in the diameter of RNA spots on the support membrane and even loss of RNA from the membrane at lower concentration. The results suggest that salt concentration is another method to adjust spot size.

EXAMPLE 5

Production of a Nucleic Acid Gauge

In the next series of experiments, Magnacharge nylon (MSI) nucleic acid-support was used. Nucleic acid solutions containing 0.01 mg/ml to 5 mg/ml was prepared in a dilution solution, pH 6.9. was used. A 1 $\mu$l aliquot from each dilution was applied to the nucleic acid-support and the spots detected as described above.

The nucleic acid solutions with higher concentrations produced larger spots than nucleic acid solutions with lower nucleic acid concentration (see FIG. 1). The diameter or size of nucleic acid spots were substantially proportional with nucleic acid amount for spots containing more than 0.0125 $\mu$g nucleic acid. Spots containing less than 0.0125 $\mu$g nucleic acid were almost identical in size and too small for measurement; however, the color intensity of the spots continued to decrease with decreasing nucleic acid concentration.

Figure 2:
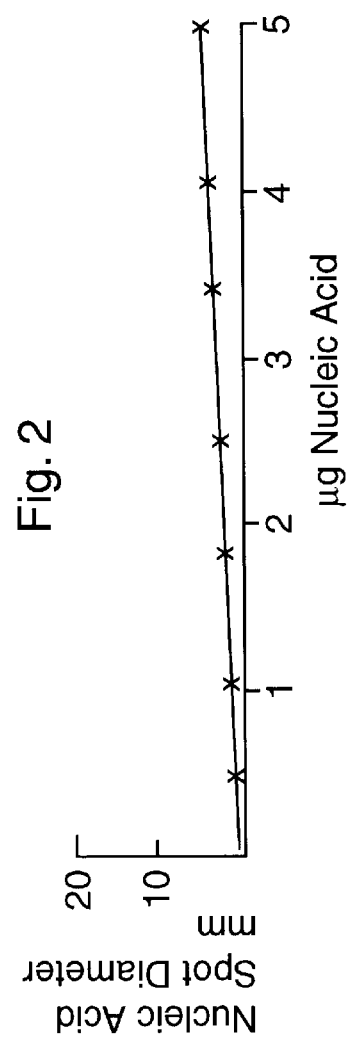
FIG. 2 shows a plot illustrating the substantially linear relationship between the diameter (mm) of the nucleic acid spots and the amount of nucleic acid ($\mu$g) in nucleic acid spots produced on a nucleic acid-support in accordance with the invention.
Figure 5:
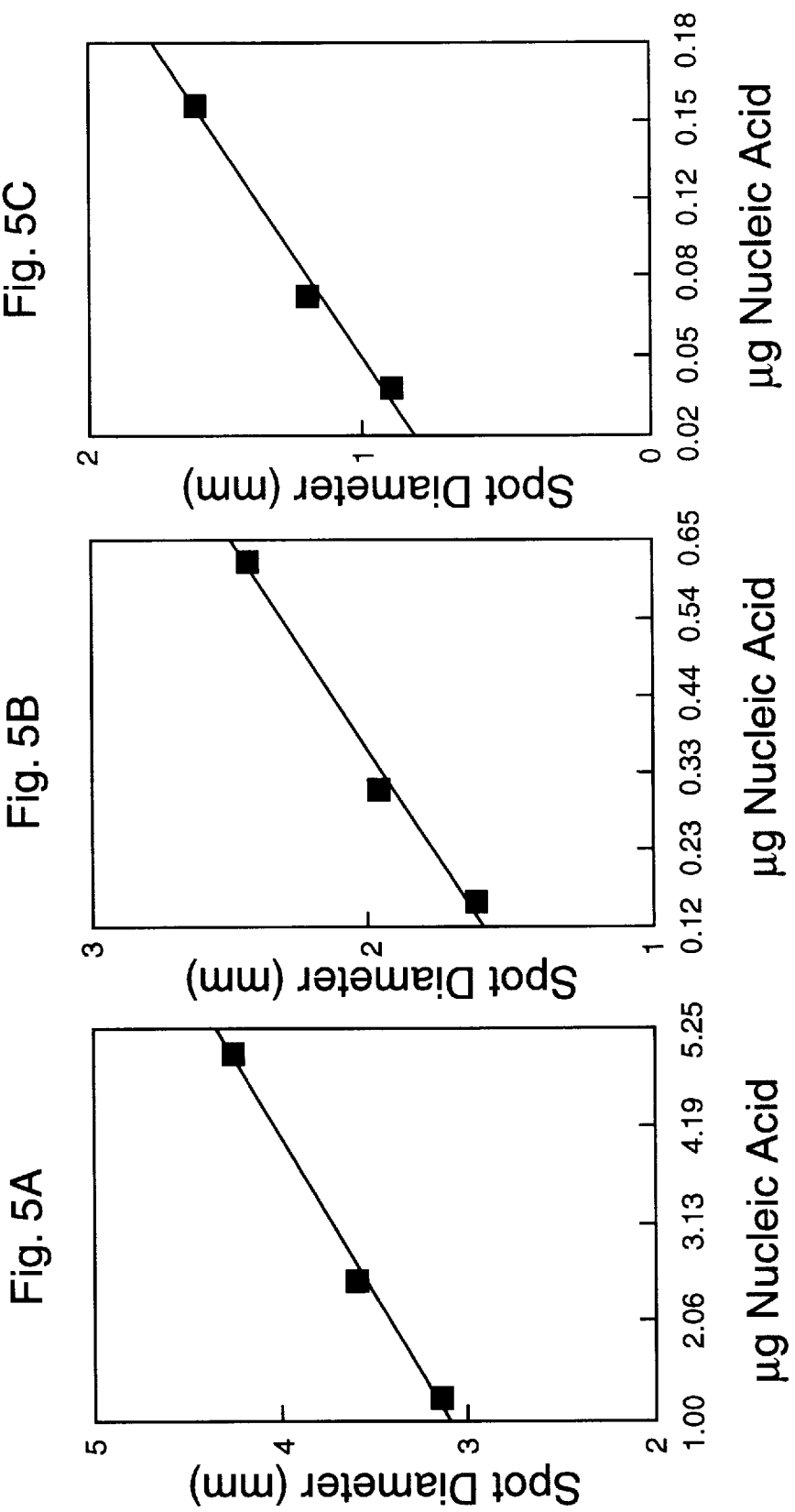
FIGS. 5A–5C shows three plots of the substantially linear relationship between the amount of nucleic acid per spot and the diameter of nucleic acid spots produced on a nucleic acid-support in accordance with the invention, with each plot A, B,and C showing a different range of nucleic acid amounts.

The diameters of nucleic acid spots produced from solutions of known nucleic acid concentrations were measured and the data obtained is recorded in Table 1. Using the diameters of a series of nucleic acid spots containing known amounts of nucleic acid a standard plot, as shown in FIG. 2, was produced. Using the plot of FIG. 2, a nucleic acid gauge, as shown in FIG. 3, was produced. The data of Table 1 was used to prepare the plot shown in FIG. 5 and the nucleic acid gauge shown in FIG. 6, both of which show the linear relationship between nucleic acid amount and diameter of nucleic acid spots. The nucleic acid gauge was transferred to a transparent sheet (10) and used to measure the diameters of nucleic acid spots and their corresponding nucleic acid amounts. To measure the amount of nucleic acid in a nucleic acid spot, the gauge was placed on the spot and a position was found where the nucleic acid spot fit between the two lines of the nucleic acid gauge and the corresponding nucleic acid amount was read (see FIG. 3)

TABLE 1

| Scale | Nucleic Acid Concentration mg/ml | Diameter m.m. |
|---|---|---|
| I | 5 | 4.25 |
|  | 2.5 | 3.76 |
|  | 1.25 | 3.13 |
| II | 0.625 | 2.41 |
|  | 0.31 | 2.07 |
|  | 0.156 | 1.6 |
| III | 0.078 | 1.30 |
|  | 0.039 | 0.90 |

Diameter of nucleic acid spots produced on a nucleic acid-binding medium made from a Magnacharge nylon membrane, obtained from MSI. Nucleic acid solutions were prepared with a dilution solution, pH 6.9, aliquots of the nucleic acid solutions were applied to the nucleic acid-support.

As will be evident to the artisan, various modifications and changes can be made to the above described embodiments and examples without departing from the spirit and scope of the instant invention. Therefore reference should be made to the claims in interpreting the breadth of the invention.

What we claim is:

1. A method for determining the concentration of nucleic acid in a nucleic acid-containing solution, comprising:

applying the nucleic acid-containing solution to a nucleic acid-support, wherein nucleic acid of the nucleic acid-containing solution contacts the nucleic acid-support in the presence of an aqueous medium having a pH effective to form a substantially uniform nucleic acid spot having a size that is proportional to the concentration of nucleic acid in the nucleic acid-containing solution;

detecting the nucleic acid spot with a nucleic acid dye, nucleic acid stain, chemiluminescent reaction or immunological reaction; and measuring the size of the nucleic acid spot; and comparing the measured size of the nucleic acid spot with a standard, thereby determining the concentration of nucleic acid in the nucleic acid-containing solution.

2. A method according to claim 1, further comprising applying nucleic acid-containing solution to the nucleic acid-support in such a manner to allow the nucleic acid-containing solution to diffuse slowly out of the pipetor tip into the nucleic acid-support.

3. A method according to claim 1, wherein the aqueous medium has a pH from 4 to 10.

4. A method according to claim 3, wherein the aqueous medium has a pH from 5.5 to 8.5.

5. A method according to claim 1, wherein the nucleic acid-support is a nylon membrane.

6. A method according to claim 1, wherein the nucleic acid-containing solution comprises a dilution of a nucleic acid sample, wherein the dilution is prepared with a dilution solution.

7. A method according to claim 6, wherein the dilution solution has a pH from 5.5 to 8.5.

8. A method according to claim 1, wherein the nucleic acid spot has a substantially circular shape and the size measured is the diameter of the spot.

9. A method according to claim 8, wherein the standard comprises a display showing a substantially linear relationship between spot diameter and nucleic acid amount for at least two substantially circular standard spots containing known, different amounts of nucleic acid.

10. A kit for determining the concentration of nucleic acid in a nucleic acid-containing solution, comprising:

a nucleic acid-support for binding and retaining nucleic acid from a nucleic acid-containing solution applied to the nucleic acid support, wherein the nucleic acid-support is capable of retaining the nucleic acid in the form of a substantially circular nucleic acid spot having a diameter that is proportional to the concentration of nucleic acid in the solution;

a means for measuring nucleic acid spot diameter, wherein said means is a gauge comprising a display which shows a substantially linear relationship between the diameter of the nucleic acid spot and the amount of nucleic acid in the spot and a calliper; and a nucleic acid detecting means selected from the group consisting of: a nucleic acid dye, a nucleic acid stain, reagents for performing a chemiluminescent reaction of reagents for performing an immunological reaction.

11. The method of claim 1 wherein said nucleic acid dye is an aqueous solution of methylene blue.

12. The method according to claim 5, wherein the nylon membrane is positively charged nylon membrane.

13. A method according to claim 6, wherein the dilution solution is comprised of a salt concentration and pH, wherein the salt concentration, the pH, or the combination of the salt concentration and the pH is effective to allow the formation of a substantially uniform nucleic acid spot.

14. The kit of claim 10, further comprising:
   a dilution solution for preparing the nucleic acid-containing solution from a sample.

15. The kit of claim 14, wherein the dilution solution is comprised of a salt concentration and pH, wherein the salt concentration, the pH, or the combination of the salt concentration and the pH is effective to allow the formation of a substantially uniform nucleic acid spot.

16. The kit of claim 10, wherein the nucleic acid-support is a nylon membrane.

17. The kit of claim 16, wherein the nylon membrane is positively charged nylon membrane.

18. The kit of claim 10 wherein said nucleic acid dye is an aqueous solution of methylene blue.

19. The kit of claim 10, wherein said means for measuring nucleic acid spot diameter is transparent.

* * * * *